United States Patent [19]

Harrison

[11] Patent Number: 5,516,407
[45] Date of Patent: May 14, 1996

[54] INDIRECT CERIUM MEDIATED ELECTROSYNTHESIS

[76] Inventor: Stephen Harrison, 600 Ave de La Moutagne, Shawinigan QC, Canada

[21] Appl. No.: 390,236

[22] Filed: Feb. 17, 1995

Related U.S. Application Data

[60] Continuation of Ser. No. 188,060, Jan. 26, 1994, abandoned, which is a division of Ser. No. 846,538, Mar. 4, 1992, Pat. No. 5,296,107.

[51] Int. Cl.$^6$ ...................................................... C25B 3/02
[52] U.S. Cl. ............................ 205/446; 205/447; 205/456
[58] Field of Search ........................... 204/78, 140, 130; 585/400; 568/326, 325, 328, 331

[56] References Cited

U.S. PATENT DOCUMENTS

| | | | |
|---|---|---|---|
| 3,413,203 | 11/1968 | MacLean | 204/86 |
| 4,312,721 | 1/1982 | Oehr | 204/78 |
| 4,313,804 | 2/1982 | Oehr | 204/93 |
| 4,536,377 | 8/1985 | Komatsu et al. | 260/396 |
| 4,632,782 | 12/1986 | Komatsu et al. | 260/396 |
| 4,639,298 | 1/1987 | Kreh et al. | 204/59 |
| 4,647,349 | 3/1987 | Kreh et al. | 204/59 |
| 4,670,108 | 6/1987 | Kreh et al. | 204/59 R |
| 4,701,245 | 10/1987 | Kreh | 204/78 |
| 4,794,172 | 12/1988 | Kreh | 534/15 |
| 5,266,173 | 11/1993 | Bandlish et al. | 204/72 |

FOREIGN PATENT DOCUMENTS

| | | |
|---|---|---|
| 1132996 | 10/1982 | Canada . |
| 1166600 | 5/1984 | Canada . |
| 1191811 | 8/1985 | Canada . |
| 0075828 | 9/1982 | European Pat. Off. . |

OTHER PUBLICATIONS

Dalrymole et al.; An Indirect Electrochemical Process for the Production of Naphthaquinone, Journal of Applied Electrochemistry, 16 (1986) 885–893.

Comninellis, CH. "Electrochemical production of ceric sulphate in concentrated $H_2SO_4$", Journal of Applied Electrochemistry, vol. 13 (1983) pp. 117–120.

Kreh, Robert P. "Selective Oxidations with Ceric Methanesulfonate and Ceric Trifluoromethanesulfonate." Tetrahedron Letters, vol. 28, No. 10, (1987) pp. 1067–1068.

Pichaichanarong, P. "Simulation of a Mediated Electrochemical Process." Chem. Eng. Comm., vol. 94 (1990) pp. 119–130.

Spotnitz, R. M. "Mediated Electrosynthesis with Cerium (IV) in Methanesulphonic Acid." Journal of Applied Electrochemistry, 90(2) (1990) pp. 209–215.

Kreh, Robert P. "Aromatic Aldehydes, Ketones and Quinones by Mediated Electrooxidation." in Genders, J. David, *Electrosynthesis From Laboratory to Pilot. to Production*, Chapter 10, (1990).

Brochure entitled: "Dished Electrode Membrane Cell" High Efficiency Electrolysis for Chemical Synthesis. Electrocatalytic, Inc.

Brochure entitled: "Seltech", including The DEM Pilot Cell, The DEM Cell (Technical Description) and The DEM Cell (Applications). Steetley Engineering Ltd.

Brochure entitled: "The EC Electro Cell Programme", ElectroCell AB.

*Primary Examiner*—Kathryn Gorgos
*Attorney, Agent, or Firm*—Limbach & Limbach; Patricia Coleman James

[57] ABSTRACT

An integrated process for oxidizing aromatic and alkyl aromatic compounds to form carbonyl containing reaction products comprising the reaction of quadravalent cerium with a reactant stream containing an aromatic or alkyl aromatic compound and using a high degree of mixing, followed by the electrolytic regeneration of the reduced cerium ion in a cell under near turbulent or turbulent flow conditions at high solution velocities relative to the anode. The preferred cell structure for accomplishing the electrolysis utilizes an turbulence promoting anode arrangement which allows for the anolyte to flow past the anode under the conditions mentioned, and a reduced area cathode whereby the anode and cathode compartments need not be separated by an ion exchange membrane.

18 Claims, 4 Drawing Sheets

INDIRECT CERIUM MEDIATED ELECTROSYNTHESIS

This is a continuation of application Ser. No. 08/188,060 filed on Jan. 26, 1994, now abandoned which is a divisional application of Ser. No. 07/846,538 filed Mar. 4, 1992, now U.S. Pat. No. 5,296,107.

BACKGROUND OF THE INVENTION

This invention relates to the indirect electrosynthesis of carbonyl containing compounds via oxidation of aromatic and alkyl substituted aromatic compounds using ceric ions. More specifically, the invention relates to a faster and more electrically efficient indirect electrochemical process for the production of carbonyl containing compounds such as naphthoquinone from starting materials such as naphthalene, in conjunction with the electrochemical regeneration of the oxidant ion.

An indirect oxidation of organic compounds using ceric ions in aqueous methanesulfonic acid is described in U.S. Pat. Nos. 4,639,298, 4,670,108 and 4,701,245 to Kreh and others. A paper which describes further work in this area is *Mediated Electrosynthesis With Cerium (IV) In Methanesulfonic Acid* by Spotnitz, et. al., J. Appl. Electrochem 90 (2) 1990, p. 209. These documents detail the advantages of using aqueous solutions of cerium methanesulfonate and methanesulfonic acid to oxidize aromatic and alkyl substituted aromatic compounds to carbonyl containing compounds by contacting the reactant compounds with the ceric methanesulfonate solution. The present invention relates to improvements in the speed and efficiency of the processes described in these documents.

Prior to the work described in the noted prior art the use of ceric ions for oxidation of such organic compounds was inefficient because of the inability to create relatively concentrated oxidizing solutions which could be electrochemically regenerated. Ceric and cerous sulfate have limited solubility, making the electrochemical regeneration process inefficient.

While the reaction of ceric solutions with polycyclic aromatic hydrocarbons has been known for some time and workers have operated the process from laboratory to pilot plant, no one has taken the process to commercial success. The capital and operating costs of the process have been too unattractive for the investment to be made. These problems stem from the plant size required to operate the process with very dilute solutions, less than 1 molar in ceric ion. Current efficiencies are low and the plant vessels are necessarily large to accommodate such a high volume of electrolyte.

The use of methanesulfonic acid described by Kreh et. al. addressed this problem to some extent, since operating concentrations were raised from 0.1 molar to 5 molar in cerium. This process improved the convenience of the procedure as the working solution was capable of oxidizing much more organic substrate before the regeneration step was required. The penalty incurred was the cost of a more expensive electrolyte and complications in the separation procedure. Additionally, the process of the prior art is not as energy efficient as would be desired. Thus, while the oxidation reactions described in the prior art brought about substantial improvements, there continues to be a need for an oxidizing process which is sufficiently fast and electrochemically efficient enough for commercialization.

SUMMARY OF THE INVENTION

In order to overcome the drawbacks of prior processes, the present invention is a process for oxidizing aromatic and alkyl aromatic compounds to form carbonyl containing reaction products comprising the reaction of quadravalent cerium with a reactant stream containing an aromatic or alkyl aromatic compound and using a high degree of mixing. In the most preferred embodiment, a static mixer is used to create turbulence in the reaction mixture. Following the reaction the reduced cerium ion is electrolytically regenerated in a cell under near turbulent or turbulent flow conditions at solution velocities relative to the anode of greater than 0.25 meters per second. The most preferred cell structure for accomplishing the electrolysis utilizes an anode arrangement which allows for the anolyte to flow past the anode under the conditions mentioned, and a reduced area cathode whereby the anode and cathode compartments need not be separated. Thus, the unique process conditions and cell design combine to achieve improved energy efficiency while lowering the cost of the cell structure itself. The combined cerium regeneration and cerium/organic reaction processes become sufficiently electrochemically efficient to reasonably allow for the commercial, continuous, production of the organic oxidation process, such as the production of naphthoquinone.

BRIEF DESCRIPTION OF THE DRAWINGS

The process of the invention will be better understood by reference to the drawing figures appended hereto of which.

DETAILED DESCRIPTION OF THE INVENTION

The basic process of the invention occurs in two distinct stages, i.e. using the so-called "indirect" oxidation method. First, oxidation of the organic reactant material with aqueous acidic solutions of ceric ion occurs, the products being oxidized organic compounds such as quinone or other carbonyl group containing compounds, and reduced cerous ion. Water is the source of oxygen in the process. Second, the reoxidation of the trivalent cerous ion to quadravalent ceric ion occurs at the anode of an electrochemical cell.

As the oxidizing solution is mixed with the organic substrate (such as naphthalene), the following reaction occurs:

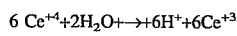

$$6\ Ce^{+4} + 2H_2O \rightarrow +6H^+ + 6Ce^{+3}$$

The regeneration reaction at the anode of the cell the reaction is:

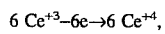

$$6\ Ce^{+3} - 6e \rightarrow 6\ Ce^{+4},$$

and at the cathode:

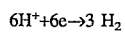

$$6H^+ + 6e \rightarrow 3\ H_2$$

As electrolysis proceeds, the cerous ion is converted to ceric, a strong oxidizing agent. Note that the acidity of the solution declines as the regeneration proceeds.

In the electrochemical regeneration step, an anomaly in the mass transfer characteristics of the process was identified which unexpectedly permits the use of less electrode surface area while nevertheless maintaining high current efficiencies. This simplifies the cell design and lowers its cost in two ways. First, electrodes are smaller and less costly. Second, in the most preferred form of the invention, the cell can be efficiently operated without an ion exchange membrane in place, eliminating a cost and ensuring operation with lower overall cell voltages.

The anomaly discovered is that the expected limiting current densities at a given concentration of cerous ion, (i.e. the current density at which the redox reaction becomes mass transfer limited and no increase in reaction rate with increased mixing would be expected), calculated using empirical formulae, do not match the measured current densities and current efficiency relationships at a given cerous ion concentrations. Thus, while it normally would be expected that the electrolysis step would be mass transfer limited, it has been found that this is not the case. Examples 1–4, below, quantify this effect.

ELECTROCHEMICAL REGENERATION OF CEROUS SOLUTION

EXAMPLE 1

Figure 4A:
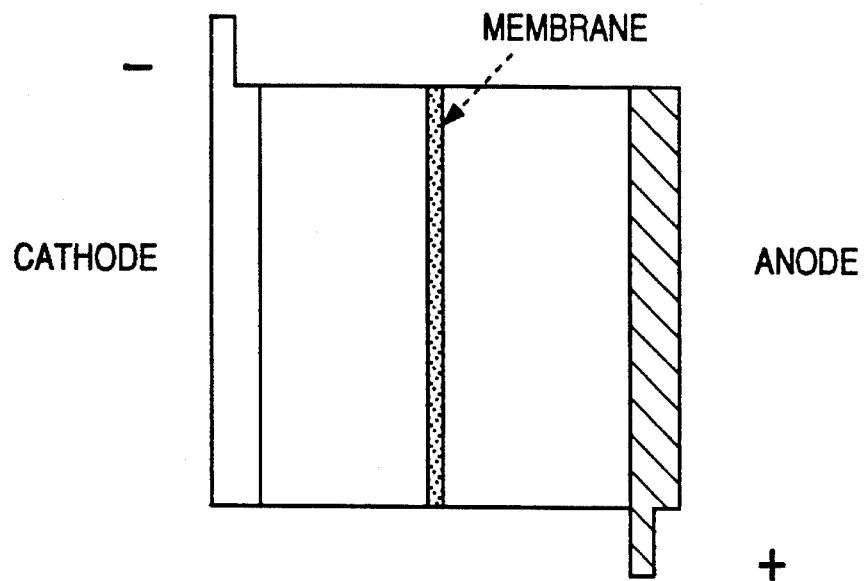
FIGS. 4A and 4B show the relevant details of the cell structure/electrode arrangement useful in the invention.
Figure 4B:

An amount of 625 parts by weight of methanesulfonic acid was added slowly to a suspension of ceric carbonate (275 parts,) in water (400 mls). After addition of all the acid carbon dioxide, evolution ceased. Additional water was added to complete the solvation. The resulting solution of cerous methanesulfonate (1.0 molar) in methanesulfonic acid (3.5 molar) was transferred to an anolyte reservoir in an electrochemical cell (Electrosyn model by Electrocell AB) consisting of a plate cathode of stainless steel and an anode of platinized titanium mesh. The anode mesh was made from a piece of expanded titanium mesh fastened to a piece of titanium sheet; both items were covered with platinum. FIG. 4A represents this arrangement. The turbulence promoting feature of the anode surface is shown in FIG. 4B. This arrangement consisted of the flat plate electrode for the "Electrosyn" cell and a piece of platinized titanium mesh (from ICI Chemicals and Polymers), held to the plate electrode using spot welding (or similar method) or by simple mechanical contact when held within a cell frame.

A similar solution was transferred to a catholyte reservoir, and the two electrolyte solutions were recirculated through the cell. An ion exchange membrane made from Nafion™ "Semi-permeable plastic membrane, placed between the anode and cathode prevented mixing of the two circulating electrolytes. A current of 160 amps, equivalent to a current density on the anode and cathode of 4000 amps per square meter, was passed through the cell while the electrolyte was circulated for a period of 240 minutes. The cell voltage was 3.8 volts. At the end of the electrolysis, a solution of ceric methanesulfonate having a concentration in ceric ion $Ce^{+4}$ of 0.66 mol/liter was produced in the electrolyte. The coulombic efficiency of this experiment was 93%. The temperature throughout the experiment was maintained at 60° C.

EXAMPLE 2

A similar solution as used in example 1 was electrolyzed in a cell where a single flow of electrolyte from only one reservoir was used. The ion exchange membrane (FIG. 4A) was replaced by a porous diaphragm made from Celgard™ polypropylene, allowing the cathode surface to be wetted. The cell voltage was 4.2 volts due to the extra resistance of the Celgard membrane and the altered conditions around the cathode. The electrolysis conditions were otherwise identical to example 1 in all other details. After 120 minutes of electrolysis, a solution of 0.44 ceric methanesulfonate was formed at a current efficiency of 90% and after 210 minutes the concentration was 0.66 molar at a current efficiency of 71%.

EXAMPLE 3

A similar electrolysis to example 2 was performed except that the Celgard diaphragm was removed and the cathode replaced with an expanded mesh of reduced surface area compared to the flat plate, i.e. having at most one-third the surface area of the flat plate (and preferably less). The inside measurements of the meshes of the cathode measure 3.5 cm by 1.6 cm. A current of 320 amperes was passed for a period of 90 minutes after which the solution contained 0.42 molar ceric ion. The current efficiency for the electrolysis of cerous to ceric was 91%. After a further 30 minutes of electrolysis, the concentration of ceric ions had risen to 0.51 molar and the current efficiency at this point was 84%.

EXAMPLE 4

Comparison-Theoretical Versus Measured Performance of Electrolytic Cell

An electrolysis similar to example 1 was completed at a lower current density (2 kA/m$^2$) and on a planar platinized titanium anode, i.e. without any screen. In this experiment, the current efficiencies were 90% after 20% conversion of cerium (III) in cerium (IV) and 70% at 50% conversion. According to the published empirical correlation for this electrochemical cell:

| | | |
|---|---|---|
| Sh = 5.57 | $Re^{0.4} Sc^{1/3}$ | where |
| | Re = vl/u | |
| | Sh = $K_L$l/D | |
| | Sc = u/D and | |
| | l = 2bh/(b+h) | |
| h = 2.5 mm (anode-membrane gap) | | |
| b = 0.144 m (width of the electrode) | | |
| $D_{Ce(III)}$ = $10^{-10}$ m$^2$/s (diffusion co-efficient) | | |
| u = 1.51 × $10^{-6}$ m$^2$/s | | |

Using this information, it is possible to calculate the expected mass transfer limited current density by using the equation $(1_{lim})$=nF$C_{Ce(III)}$ $K_L$, where $C_{Ce(III)}$ is in kmol/m3. The mass transfer coefficient $K_l$ can be calculated from the aforementioned correlation, and hence, the mass transfer limited current densities can be calculated.

In the present case, at a concentration of 0.5M cerous methanesulfonate, the expected (calculated) mass transfer limited current density should be 2.5 kA/m$^2$, and at a 1.0M the limiting current density should be 5 kA/m$^2$. It is, therefore, surprising that the experimentally determined current efficiencies noted above are not 100% at these concentrations of cerium (III), since the experiment was run at well below the calculated mass transfer limited current density. It is even more surprising that when the surface area of the anode (as in example 1) is increased there is still an influence of mass transfer albeit at higher current densities, as shown in FIG. 3.

Figure 3:
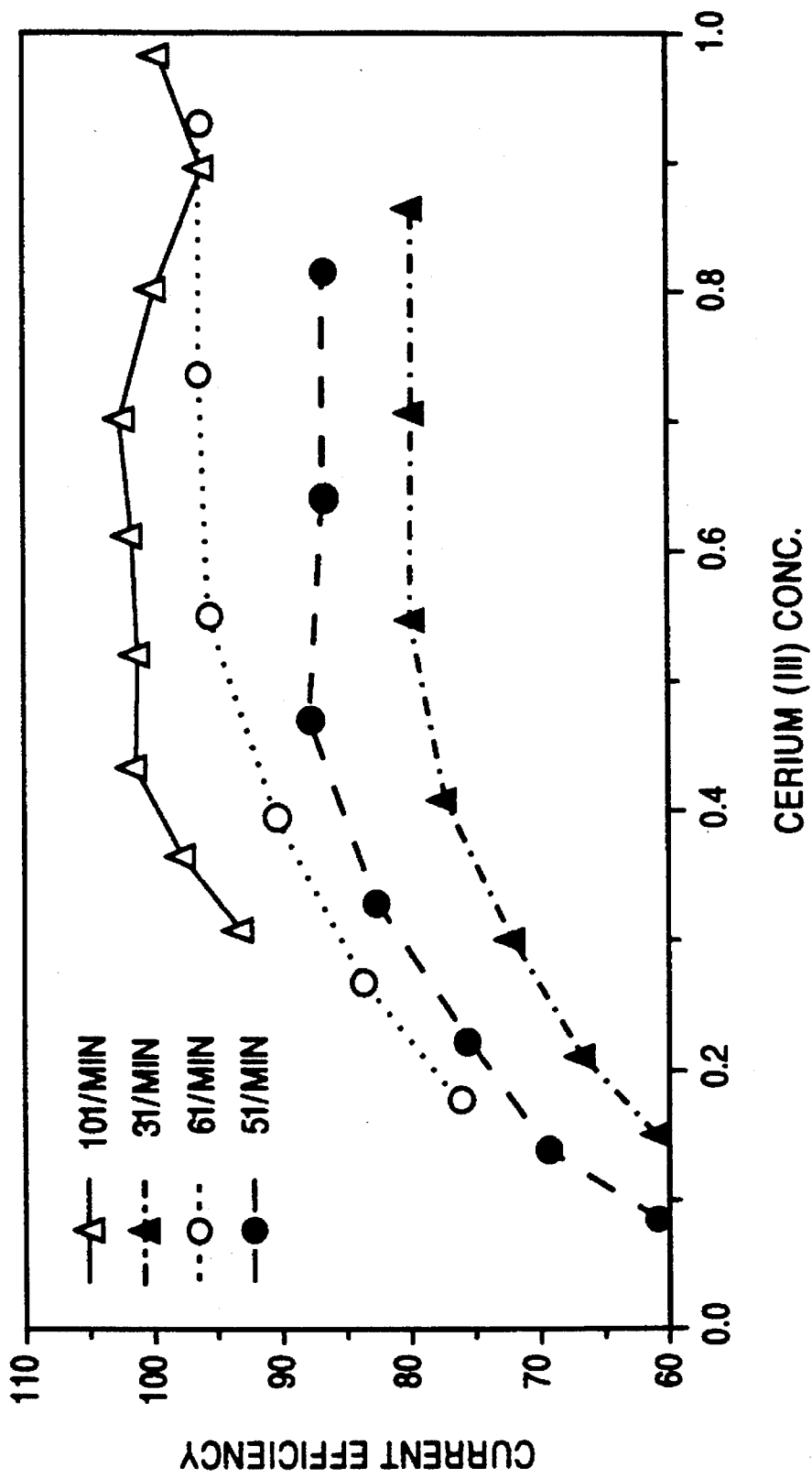
FIG. 3 is a graph depicting the measured effect of changes in cerium (III) concentration on current efficiency in the electrolysis step of the process.

In FIG. 3, the affect of cerium III concentration is shown on current efficiency, at various flow rates through the cell. Based on the particular geometry of the cell, the following solution velocities correlate to the volumetric flow rates shown.

| Flow Rate (l/min) | Velocity (m/s) |
|---|---|
| 3 | 0.14 |
| 5 | 0.23 |
| 6 | 0.28 |
| 10 | 0.46 |

At the velocities shown, it appears that the cell approaches turbulent flow at a solution velocity of about 0.28. It is estimated that the mass transfer anomaly identified begins to occur at about this solution velocity. What appears to be most important is that the conditions of flow are at near turbulent or turbulent flow and that the solution velocity is great enough to create high rates of mass transfer to the electrode surface. As can be seen from FIG. 3, if the flow becomes much less than 0.28 m/sec past the anode, the current efficiencies at any given cerium concentration fall below the level necessary to maintain economic operation of the cell. It may be noted that prior art systems operated at maximum solution velocities of about 0.15 m/sec.

PRODUCTION OF NAPHTHOQUINONE

EXAMPLE 5

Figure 1:
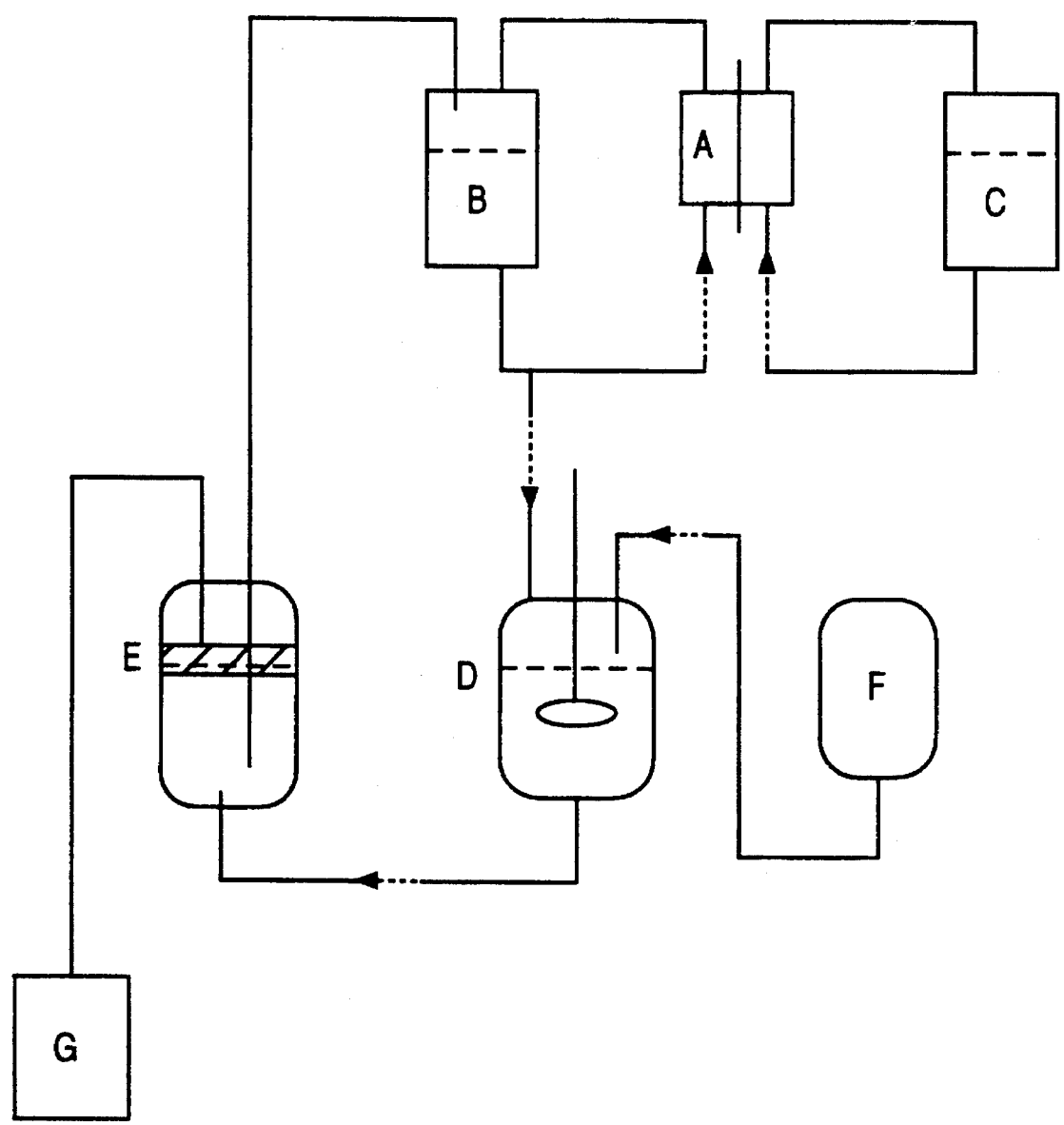
FIG. 1 is a diagram showing an arrangement of process vessels allowing for operation of the method of the invention.

A similar electrolysis to that described in example 1 was stopped after 180 minutes, and a solution of 0.43M ceric methanesulfonate was produced at a current efficiency of 95%. A portion of this solution (1000 parts) was transferred to a laboratory reactor D of FIG. 1. The solution was reheated to 60° C. At this point, 250 parts of a 0.2 molar solution of naphthalene dissolved in 1,2-dichloroethane was added to the ceric solution from tank F and the mixture agitated at 2200 rpm by using a mechanical paddle blade agitator. After 5 minutes, the oxidation of the naphthalene to naphthoquinone was 99.3% by analysis of an aliquot taken from the reaction. The selectivity to naphthoquinone was calculated to be 98% and an overall current efficiency for the ceric solution of 95%. After a further 5 minutes, the reaction was stopped and the conversion was complete. Melting point determination of the product recovered from the solvent gave a melting point of 124°–6° C. compared to a commercial product with a melting point of 122°–124° C., thus indicating a very pure naphthoquinone product.

EXAMPLE 6

Continuous Production

Figure 2:
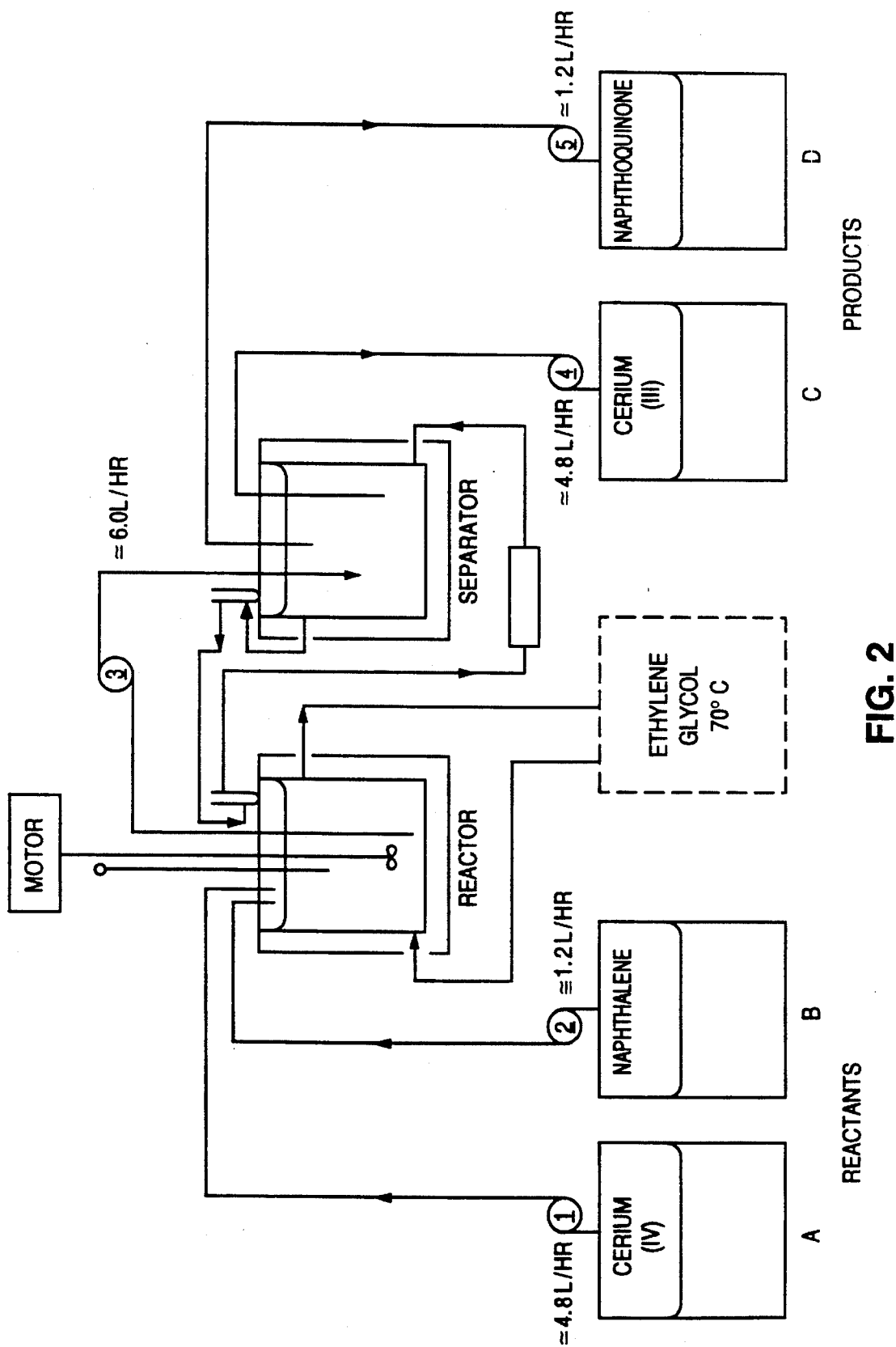
FIG. 2 is a diagram of an alternative arrangement of vessels suitable for continuous operation of the method of the invention.

A second portion of the solution described in example 1 was transferred to the reservoir A in FIG. 2. Reservoir B contained a solution of naphthalene 0.2 molar, in 1,2 dichloroethane solvent. The pilot plant was assembled such that additional quantities of ceric solution as described in example 1 could be added to the reactor. The solution in the reactor was heated to 60° C., 0.25 liters of the solution from reservoir B was added to the reactor. At this time, pumps 1,2, and 3 were started; the rate of pumping was adjusted such that a residence time of 20 minutes was achieved at a constant ratio of organic phase (naphthalene in 1,2 dichloroethane) to aqueous of 4:1. In the separator, in FIG. 2, the reaction product formed two distinct and separate layers with the organic phase at the top. At the point where the separator became ¾ full, pumps 4 & 5 were started and set to maintain a constant level in the separator. The aqueous cerous $Ce^{+3}$ solution at the bottom of the separator was pumped to reservoir C, and the naphthoquinone product solution was pumped to reservoir D. During a period of several hours of continuous operation, the results of analysis on aliquots taken from the process showed a conversion of naphthalene to naphthoquinone of 90%, a yield of naphthoquinone of 96% and a cerium selectivity of 96%. In these experiments, agitation was reduced to 1200 rpm.

EXAMPLE 7

Continuous Production

The equipment (FIG. 1) included electrochemical cell A, recirculation reservoirs for anolyte and catholyte B & C, a jacketed chemical reactor D, phase separator E, and feed and product reservoirs F & G respectively. A solution of cerous methanesulfonate (0.43 Molar) was prepared and transferred to D, further quantities of cerous methanesulfonate were prepared as in example 1. A solution of pre-electrolyzed cerous/ceric solution (0.13/0.87M) was transferred to E. Naphthalene (0.2M) dissolved in 1,2 dichloroethane was transferred to F. The solutions in the reservoirs B, C and D were preheated to the operating temperature of 60° C. Once the operating temperature was stabilized, the anolyte and catholyte solutions were circulated through the cell. A current of 320 amps (equivalent to a current density of 4000 amps per square meter) was applied from a controlled rectifier power supply unit. At the same time, a solution of naphthalene, 0.2 molar in naphthalene was dissolved in 1,2 dichloroethane, was transferred to D and the agitation started (600 rpm). Subsequently, the anolyte was pumped along with the solution from the reservoir F into D. As D and E are connected hydrostatically, they maintain an equivalent level. The ceric methanesulfonate solution from E is pumped at a rate to maintain constant level in D and E. At the time when adequate phase separation was observed in the reactor (5–10 minutes), the organic phase was transferred to G. The solutions are transferred to D and E at such a rate to maintain a residence time of 33 minutes. The experiment was operated for a period of 6.5 hours. Throughout this electrolysis, the current efficiency for the oxidation of cerous to ceric ion was maintained between 90–99%, the coloumbic efficiency for the conversion of naphthalene to naphthoquinone was 94.5% and the chemical yield of naphthoquinone varied between 90 and 100%.

EXAMPLE 8

Continuous Production—Increased Agitation in Reactor

Under similar conditions to example 7 but with a higher degree of agitation (700 rpm), the residence time was 25 minutes. The current efficiency and yield of naphthoquinone were 93% and 91%, respectively, and the naphthalene conversion was 98%.

EXAMPLE 9

Use of Static Mixer

A solution from example 1 was pumped at a rate of 40 l/h with a solution of 0.2M naphthalene in 1,2-dichloroethane at a rate of 10 l/h into a static mixer reactor of length 12 cm and of cross sectional area of 0.69 cm². At the exit of the reactor, some 10% of the naphthalene was converted into naphthoquinone with a selectivity of 100%. It is preferred to use a plug flow reactor for this reaction, having turbulence promotors therein as this creates a uniform particle size and creates an additional surface for the reaction to take place.

DISCUSSION

The advantages achieved by the invention as compared with prior processes can be seen in Table 1.

TABLE 1

| Figures of Merit | Prior art | Present work | Comments |
|---|---|---|---|
| Cell volt. @ 4 kA/m² | 5–6 volts | 3.5 volts | |
| Energy consump. kWh/Kg @ 5 kA/M² | 5.0 | 3.5 | Earlier work 6–7, using dilute solutions |
| Cell productivity Kg/h/M² | 3.36 | 3.36 | Electrode prod 5× better in latest work |
| Naphthalene reaction time to 100% conversion | 30 minutes | 10 minutes | older work up to several hours |

In example 1, using a divided cell fitted with a membrane, the coulombic efficiency and cell voltage combine to achieve an energy consumption for the process for ceric oxidation of 3.5 kW/kg at 4 kA/m² a figure better than 43% superior to any prior art. This was achieved by increased flow through the cell and a small cell gap (5 mm in this example). The high current efficiency of 93% was achieved on a smaller electrode.

In experiments 2 and 3, the membrane was removed, thereby simplifying the process by removing the need for a catholyte recirculating system including pump and electrolyte tank. This also simplifies electrolyte maintenance, a problem with redox systems as the solution becomes unbalanced due to migration of ions and water. In the case of example 3, the separator was removed altogether and a reduced surface area cathode inhibited the reduction of ceric ion. This gave the best economics as the cell voltage reached a minimum and the loss of current efficiency was only marginal. Special electrodes were tested for this duty and included titanium metal, Magneli phase titanium suboxides and Hastalloy C.

Example 4 highlights the mass transfer anomaly identified, whereby increased turbulence and solution velocity within the cell during electrolysis improves the conversion of cerium III to cerium IV ion, even though empirical cell calculations clearly show no such increase would be expected. As noted in example 4, FIG. 3 shows this effect. The process also allows the use of fewer anode meshes under the conditions described in the prior art, thereby lowering the cost of the anode.

In the second part of the process, concerning the mixing of the ceric solution with the organic substrate, in the main case naphthalene dissolved in various water immiscible solvents such as chlorobenzene, dichlorethane or benzene, it was found that the reaction rates were dependant on the degree of mixing of the two phases. Significant improvement was made in this part of the process. It should be noted, however, that the degree of mixing is limited by the finding that overmixing of two immiscible solvents can lead to the formation of emulsions which are very difficult to handle.

It has been found that increasing the shear in the mixing of the two reactant solutions (whether this is achieved by faster stirring or the design of the baffles in the mixing tank) reduces the time for complete reaction by a factor of three. Emulsion formation is kept to a manageable minimum by ensuring the solutions contain no suspended solids. To this end, the solutions are filtered prior to mixing. Any emulsion formed can be broken by filtration.

The net result of this finding is that the reaction time now reaches a level where a continuous process can be designed using a tube reactor or a cascade of reactors to give a total residence time of ten minutes during which all the naphthalene is converted to naphthoquinone. In the most preferred form, this is achieved using a plug flow reactor having turbulence promotors therein as shown in example 9 above.

While the present invention has been described with respect to the production of naphthoquinone, it should be noted that the invention has broader applicability in practice. As those skilled in the art will understand, many other reactions will be likewise made more efficient; for example, the reaction of anthracene to anthraquinone, pyrene to pyrenequinone, and the same reactants carrying groups such as nitro, methyl and paraffin chains. The cerium electrosynthesis process can be used not only in connection with the production of quinones, but is also useful in any process where cerium can effectively be used as an oxidant, and then regenerated, for example in the oxidative destruction of organic materials considered to be toxic (such as dyestuff residues, pesticides and animal by-products) in effluent streams.

What is claimed is:

1. A process for oxidizing aromatic and alkyl aromatic reactants to form carbonyl-containing reaction products comprising the steps of:

(a) preparing an aqueous solution of cerium$^{III}$ in methanesulfonic acid;

(b) in an electrochemical cell, electrolytically converting said cerium$^{III}$ in said aqueous solution to cerium$^{IV}$ to form an aqueous reactant solution of cerium$^{IV}$ in methanesulfonic acid;

(c) transferring said aqueous reactant solution from said cell to a plug flow reactor; and (d) mixing, in said plug flow reactor, said aqueous reactant solution with a water immiscible organic solution containing a solubilized aromatic or alkyl aromatic reactant in said water immiscible organic solution to form a carbonyl-containing reaction product and cerium$^{III}$.

2. A process for oxidizing aromatic and alkyl aromatic reactants to form carbonyl containing reaction products comprising the steps of:

(a) preparing a solution of cerium$^{III}$ in methanesulfonic acid;

(b) in an electrochemical cell, electrolytically converting said cerium$^{III}$ to cerium$^{IV}$ to form a reactant solution of cerium$^{IV}$ in methanesulfonic acid;

(c) transferring said reactant solution from said cell to a plug flow reactor; and (d) reacting, in said plug flow reactor, an aromatic or alkyl aromatic reactant in said reactant solution to form a carbonyl containing reaction product and cerium$^{III}$.

3. A process according to claim 2 comprising the further steps of:

(e) separating said cerium$^{III}$ from said reaction product; and (f) recycling said separated cerium$^{III}$ to step (b) for continued processing.

4. A process according to claim 2, wherein said reactant is selected from the group consisting of naphthalene, anthracene and pyrene.

5. A process according to claim 2, wherein said reactant is naphthalene.

6. A process according to claim 2, wherein step (d) includes the further step of agitating said reaction mixture.

7. A process according to claim 6, wherein said further step of agitating is accomplished without forming an emulsion in said reaction vessel.

8. A process according to claim 6, wherein said agitation step is accomplished using a static mixer.

9. A process for oxidizing aromatic and alkyl aromatic reactants to form carbonyl-containing reaction products, comprising the steps of:

(a) preparing an aqueous solution of cerium$^{III}$ in methanesulfonic acid;

(b) in an electrochemical cell, electrolytically converting said cerium$^{III}$ to cerium$^{IV}$ to form an aqueous reactant solution of cerium$^{IV}$ in methanesulfonic acid;

(c) removing said reactant solution from said cell to a plug flow reactor;

(d) combining a water immiscible organic phase in said plug flow reactor with said aqueous solution, said organic phase comprising a solubilized aromatic or alkyl aromatic reactant; and (e) flowing a combination of said organic phase and said reactant solution formed in step (d), during plug flow, through turbulence promotors in said plug flow reactor to cause said solubilized aromatic or alkyl aromatic reactant to react with said cerium$^{IV}$ and form a product stream including a carbonyl-containing product and cerium$^{III}$.

10. A process according to claim 9 further comprising the steps of:

(e) separating said cerium$^{III}$ from said product stream; and (f) recycling said separated cerium$^{III}$ to step (b) for continued processing.

11. A process according to claim 9, wherein said reactant is selected from the group consisting of naphthalene, anthracene and pyrene.

12. A process according to claim 9, wherein said organic phase is selected from a member of the group consisting of dichloroethane, benzene and chlorobenzene.

13. A process according to claim 9, wherein said water immiscible organic phase and said aqueous solution are each filtered to remove suspended solids prior to the combining of these streams in step (c).

14. A process for oxidizing napthalene to form napthoquinone, comprising the steps of:

(a) preparing an aqueous solution of cerium$^{III}$ in methanesulfonic acid;

(b) in an electrochemical cell, electrolytically converting said cerium$^{III}$ to cerium$^{IV}$ to form an aqueous solution of cerium$^{IV}$ in methanesulfonic acid;

(c) forming a reactant stream comprising napthalene dissolved in a water immiscible organic solvent;

(d) mixing a combination of said reactant stream and said aqueous solution in a plug flow reactor to cause said napthalene to react with said cerium$^{IV}$ and form a product stream including napthoquinone and cerium$^{III}$.

15. A process according to claim 14 further comprising the steps of:

(e) separating said cerium$^{III}$ from said product stream; and (f) recycling said separated cerium$^{III}$ to step (b) for continued processing.

16. A process according to claim 14, wherein step (d) comprises the further step of passing said combination through turbulence promotors in said plug flow reactor.

17. A process according to claim 14, wherein said reactant stream comprises 0.2M napthalene in 1,2-dichloroethane.

18. A process according to claim 14, wherein said reactant stream and said aqueous solution are each filtered to remove suspended solids prior to the combining of these streams in step (d).

* * * * *

UNITED STATES PATENT AND TRADEMARK OFFICE
CERTIFICATE OF CORRECTION

PATENT NO. : 5,516,407
DATED : May 14, 1996
INVENTOR(S) : Stephen Harrison

It is certified that error appears in the above-identified patent and that said Letters Patent is hereby corrected as shown below:

On the title page, enter the following: [73] Assignee: HYDRO-QUEBEC, Montreal, Canada On the title page, item [76] should read --Stephen Harrison, 600 Ave. de la Montagne, Shawinigan, QC, Canada--.

Signed and Sealed this

Thirty-first Day of August, 1999

Attest:

Q. TODD DICKINSON

*Attesting Officer*  *Acting Commissioner of Patents and Trademarks*